(12) United States Patent
Propp et al.

(10) Patent No.: US 7,674,948 B2
(45) Date of Patent: *Mar. 9, 2010

(54) WINDOW DRESSING

(75) Inventors: Donald J. Propp, Dewitt, MI (US); Curtis L. Carpenter, Williamston, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/977,757

(22) Filed: Oct. 26, 2007

(65) Prior Publication Data

US 2008/0058692 A1 Mar. 6, 2008

Related U.S. Application Data

(62) Division of application No. 11/209,888, filed on Aug. 23, 2005, now Pat. No. 7,294,751.

(51) Int. Cl.
*A61F 13/00* (2006.01)
(52) U.S. Cl. .............. 602/58; 602/41; 602/42; 602/43; 602/52; 602/54; 604/180
(58) Field of Classification Search ............. 604/41–59, 604/179, 180; 602/41–59; 128/888, 889; D24/189
See application file for complete search history.

(56) References Cited

U.S. PATENT DOCUMENTS

| 6,124,520 | A | * | 9/2000 | Roberts | 602/54 |
| 6,140,548 | A | * | 10/2000 | Hansen et al. | 602/57 |
| 6,967,261 | B1 | * | 11/2005 | Soerens et al. | 602/48 |
| 7,294,752 | B1 | * | 11/2007 | Propp | 602/58 |
| 2004/0220505 | A1 | * | 11/2004 | Worthley | 602/54 |

* cited by examiner

*Primary Examiner*—Kim M Lewis
(74) *Attorney, Agent, or Firm*—Fildes & Outland, P.C.

(57) ABSTRACT

A self-adherent window dressing includes a fabric layer bounded by an edge. The fabric layer has an adhesive side, an opposite non-adhesive side, and an opening therein to allow for viewing therethrough. A reinforcement member is adhered to at least a portion of the fabric layer. A transparent film layer closes the opening and has first and second opposing sides. The film layer first side is non-adhesive and is mounted on the fabric layer adhesive side to close the opening in the fabric layer. The film layer second side has a skin adhering adhesive portion and an adhesive-free portion. The adhesive-free portion is disposed inwardly of the opening. The film layer adhesive-free portion is adapted not to stick to a wound, connector, or catheter disposed between the film layer adhesive-free portion and skin.

16 Claims, 4 Drawing Sheets

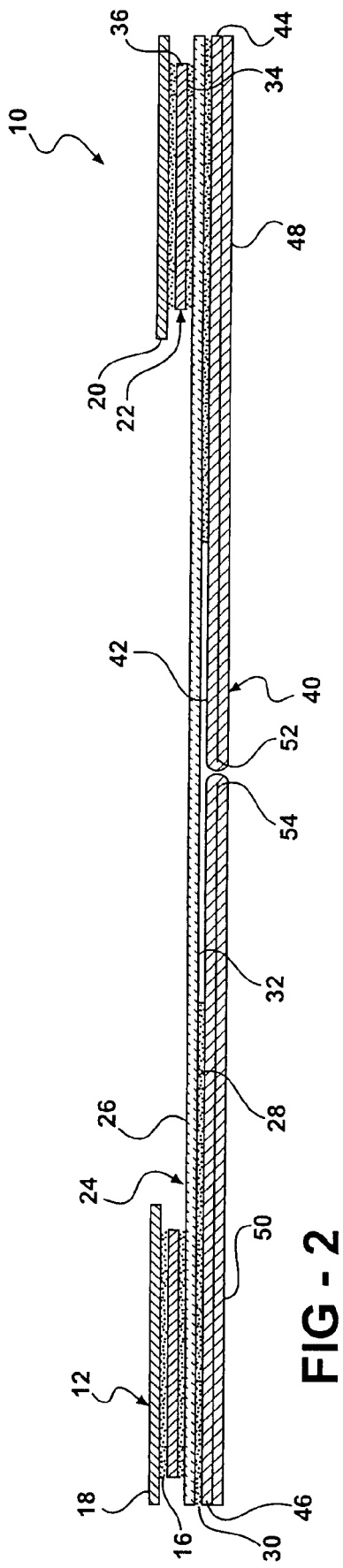
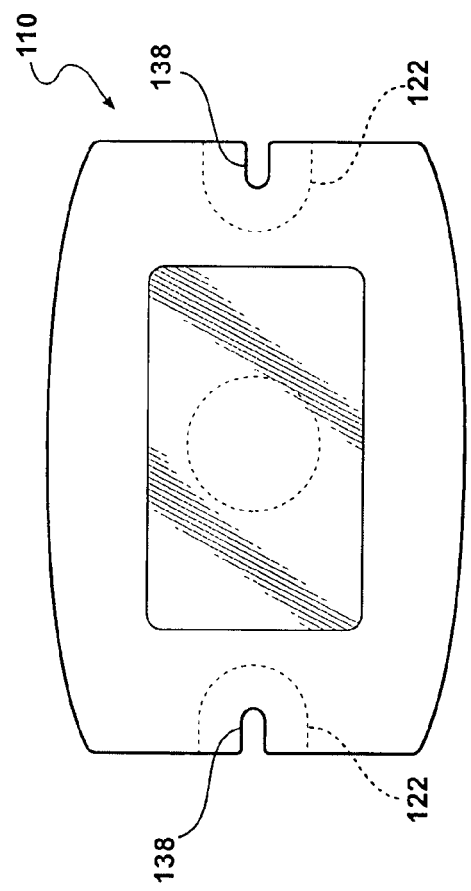

WINDOW DRESSING

CROSS REFERENCE TO RELATED APPLICATION

This application is a division of U.S. application Ser. No. 11/209,888 filed Aug. 23, 2005 now U.S. Pat. No. 7,294,751.

TECHNICAL FIELD

This invention relates to medical dressings, and more particularly to self-adherent window dressings for the protection, securement, and viewing of indwelling catheters, infusion needles, implanted port huber access needles and medical tubing about an insertion site.

BACKGROUND OF THE INVENTION

It is known in the art relating to dressings for the protection and securement of catheters and infusion needles to use self-adherent dressings to cover all or part of the insertion site. Even more simply, often medical grade tape is used to secure catheters and infusion needles to a patient, as well as to secure medical tubing extending from the catheter or infusion needle. The adhesive on tape or conventional dressings, however, often sticks to medical apparatus such as catheters, connectors, tubing, etc., rendering removal of the tape or dressing difficult. This is problematic because dressings/tape often have to be replaced before indwelling catheters or infusion needles are finished being used. When the adhesive sticks to the medical apparatus, it can cause damage to the medical apparatus as well as the insertion site or vein or artery, upon removal of the dressing, requiring relocation of the medical apparatus, or other medical intervention.

Furthermore, medical tubing connected to indwelling catheters, infusion needles and the like is often subjected to inadvertent but significant pulling forces either caused directly by patient movement or by snagging of the tubing on other objects. These pulling forces peel the medical tape or dressing securing the tubing and/or catheter, infusion needle, etc. off of the patient's skin. This undesirably exposes the catheter, infusion needle, etc. to movement inward or outward, increasing the likelihood that the catheter, infusion needle, etc. will fail and have to be replaced and inserted into a new insertion site. Also, this may weaken the adhesion between the dressing and the patient's skin, potentially exposing the insertion site to harmful bacteria.

SUMMARY OF THE INVENTION

The present invention provides a self-adherent medical window dressing that permits visual inspection of an insertion site. The window dressing includes a non-adhesive portion that will not stick to catheters, infusion needles, etc. that are protected by the dressing, allowing for easy removal and replacement of the dressing without damaging the catheter, infusion needle, or ultimately the insertion site itself. Furthermore, the present window dressing may include a reinforcement layer that increases the resistance of the dressing from peeling away from a patient's skin caused by, for example, pulling forces exerted by medical tubing.

More specifically, a self-adherent window dressing in accordance with the present invention includes a fabric layer bounded by an edge. The fabric layer has an adhesive side, an opposite non-adhesive side, and an opening therein to allow for viewing therethrough. The dressing further includes a reinforcement member adhered to at least a portion of the fabric layer, and a transparent film layer closing the fabric layer opening and having first and second opposing sides. The film layer first side is non-adhesive and is mounted on the fabric layer adhesive side to close the opening in the fabric layer. The film layer second side has a skin adhering adhesive portion and an adhesive-free portion. The adhesive-free portion is disposed inwardly of the opening. The film layer adhesive-free portion is adapted not to stick to a wound, connector, catheter, infusion needle, infusion needle safety guard, or the like disposed between the film layer adhesive-free portion and skin.

Optionally, the film layer adhesive-free portion may be generally centered within the opening. The adhesive-free portion may have one of a circular, oval, or rectangular shape.

The film layer may generally extend to, or beyond, the fabric layer edge. The reinforcement member may be a continuous strengthening layer extending around a periphery of the dressing. Alternatively, the reinforcement member may be a strengthening layer locally disposed about a portion of the dressing. The reinforcement member may be made of a netting material or similar reinforcing material with very low elasticity properties. The reinforcement member may also be disposed between the opening and the fabric layer edge. The dressing may also include a plurality of reinforcement members.

The dressing may further include at least one tubing exit recess in the fabric and/or film layer edge and the reinforcement member may be disposed about the at least one recess. The dressing may also include a release liner having a releasable side contacting the film layer skin adhesive portion, the release liner generally extending to the film layer skin adhesive portion edge. Optionally, the release liner may include a first piece and a second piece that are folded such that each of the first and second pieces have a convenient grab tab formed by the fold. One of the pieces is releasable from the dressing without tampering with the other of the pieces.

In an alternative embodiment, a self-adherent window dressing in accordance with the present invention includes a fabric layer bounded by an edge. The fabric layer has an adhesive side, an opposite non-adhesive side, and an opening therein to allow for viewing therethrough. The dressing also includes a reinforcement member adhered to at least a portion of the fabric layer and a transparent film layer closing the opening. The film layer has first and second opposing sides. The film layer first side is non-adhesive and is mounted on the fabric layer adhesive side. The film layer second side includes a skin adhering adhesive thereon.

Optionally, the reinforcement member may be a continuous strengthening layer extending around a periphery of the dressing. Alternatively, the reinforcement member may be a strengthening layer locally disposed about a portion of the dressing; generally at a tubing exit location. Further, the reinforcement member may be disposed between the opening and the fabric layer edge. The dressing may also include a plurality of reinforcement members and at least one recess in the fabric layer edge. The reinforcement member(s) may be disposed about the at least one recess.

In another alternative embodiment, a self-adherent window dressing in accordance with the present invention includes a fabric layer having an adhesive side, an opposite non-adhesive side, and an opening therein to allow for viewing therethrough. The dressing also includes a transparent film layer closing the opening and having first and second opposing sides. The film layer first side is non-adhesive and is mounted on the fabric layer adhesive side to close the opening in the fabric layer. The film layer second side has a skin adhering adhesive portion and an adhesive-free portion. The adhesive-free portion is disposed inwardly of the opening. The film layer adhesive-free portion is adapted not to stick to a wound, connector, catheter, infusion needle, infusion needle safety guard, or the like disposed between the film layer adhesive-free portion and skin.

These and other features and advantages of the invention will be more fully understood from the following detailed description of the invention taken together with the accompanying drawings.

BRIEF DESCRIPTION OF THE DRAWINGS

In the drawings:

FIG. 2 is a side cross-sectional view of the window dressing of FIG. 1;

FIG. 4 is a plan view of an alternative embodiment of a window dressing in accordance with the present invention.

DETAILED DESCRIPTION OF THE INVENTION

Figure 1:
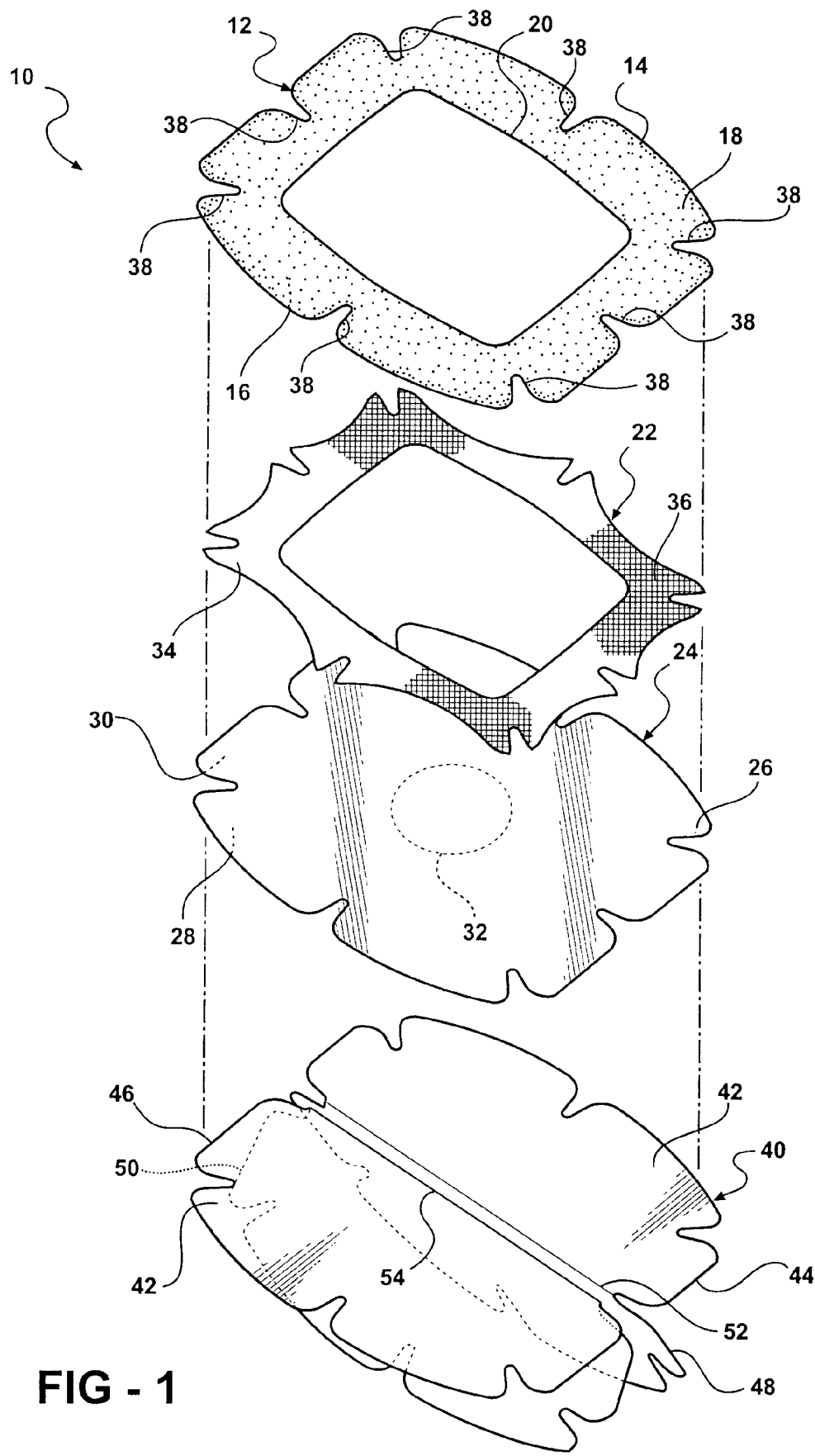
FIG. 1 is an exploded view of a window dressing in accordance with the present invention.

Referring now to the drawings in detail, numeral 10 generally indicates a self-adhering window dressing in accordance with the present invention. The window dressing includes an adhesive-free portion inwardly disposed relative to the window that allows for easy removal of the dressing without damage to or disturbance of the insertion site itself or to the catheter, infusion needle, infusion needle safety guard, or the like protected by the dressing. The window dressing may also resist edge peel forces exerted by medical tubing secured by the dressing.

Turning first to FIGS. 1 and 2, a self-adherent window dressing 10 in accordance with the present invention includes a fabric layer 12 bounded by an edge 14. The fabric layer 12 has an adhesive side 16, an opposite non-adhesive side 18, and an opening 20 therein to allow for viewing therethrough. The adhesive on the fabric layer adhesive side 16 may be a medical grade adhesive or similar. The dressing 10 further includes a reinforcement member 22 adhered to at least a portion of the fabric layer 12, and a transparent film layer 24 closing the fabric layer opening 20 and having first and second opposing sides 26, 28 respectively.

In the illustrated embodiment, the reinforcement layer 22 is generally of the same shape as the fabric layer 12, including a similar opening. The reinforcement layer 22 need not be of this configuration. The reinforcement member 22 may also have an adhesive side 34 and an opposite non-adhesive side 36, and the non-adhesive side 36 may be adhered to the fabric layer adhesive side 16.

The film layer first side 26 is non-adhesive and is mounted on part of the fabric layer adhesive side 16 as well as the reinforcement member adhesive side 34 to close the opening 20 in the fabric layer 12 and the opening in the reinforcement layer 22. The film layer second side 28 has a skin adhering adhesive portion 30 and an adhesive-free portion 32. The adhesive portion 30 may include a medical grade adhesive similar to the adhesive used for the fabric layer 12. The adhesive-free portion 32 of the film layer 24 is disposed inwardly of the opening 20. The film layer adhesive-free portion 32 is adapted not to stick to a wound, connector, catheter, infusion needle, infusion needle safety guard, or the like disposed between the film layer adhesive-free portion and skin.

Optionally, the film layer adhesive-free portion 32 may be generally centered within the opening 20, though it is equally within the scope of the invention for the adhesive-free portion 32 to be offset from the center of the opening 20. The adhesive-free portion 32 may also have one of a circular, oval, or rectangular shape, although no particular or specific shape is required by the invention. The adhesive-free portion 32 may even have an irregular shape. The adhesive-free portion 32 merely should have a shape and size that can surround the periphery of a catheter hub, connector fitting, infusion needle, safety guard, insertion site, wound, etc. covered by the dressing 10 so as to prevent damage when the dressing is removed. Further, the film layer adhesive portion 30 may be located between the adhesive-free portion 32 and the edge of the opening 20, or extend out to and/or beyond, the outer edge 14.

The film layer 24 may generally either extend fully, or partially to the fabric layer edge 14. The reinforcement member 22 may be a continuous strengthening layer extending around a periphery of the dressing 10. The reinforcement member 22 may be made of a netting material, a mesh, or other similar material with low elasticity properties. The reinforcement member 22 may also be disposed between the opening 20 and the fabric layer edge 14. It may alternatively be coincident with opening 20 and edge 14.

The dressing 10 may further include at least one recess 38 in the fabric layer edge 14 and the reinforcement member 22 may be disposed about or coincident with, the at least one recess 38. The recess 38 is sized to receive medical tubing in order to aide in securing medical tubing exiting from underneath the dressing 10, and reducing dressing edge peel.

The dressing 10 may also include a release liner 40 having a releasable side 42 contacting the film layer skin adhesive portion 30. The release liner 40 generally extends to the fabric layer edge 14. The releasable side 42 may be silicone coated or may have a similar coating. Optionally, the release liner 40 may include a first piece 44 and a second piece 46 that are folded such that each of the first and second pieces have a tab 48, 50 formed by the fold 52, 54. One of the pieces is releasable from the dressing without tampering with the other of the pieces. This allows for exposure of part of the film layer adhesive portion 30 for placement over tubings and apparatus and on part of the skin of a patient while the other part of the film layer adhesive portion remains covered so it cannot prematurely stick to the skin or to itself.

Figure 3:
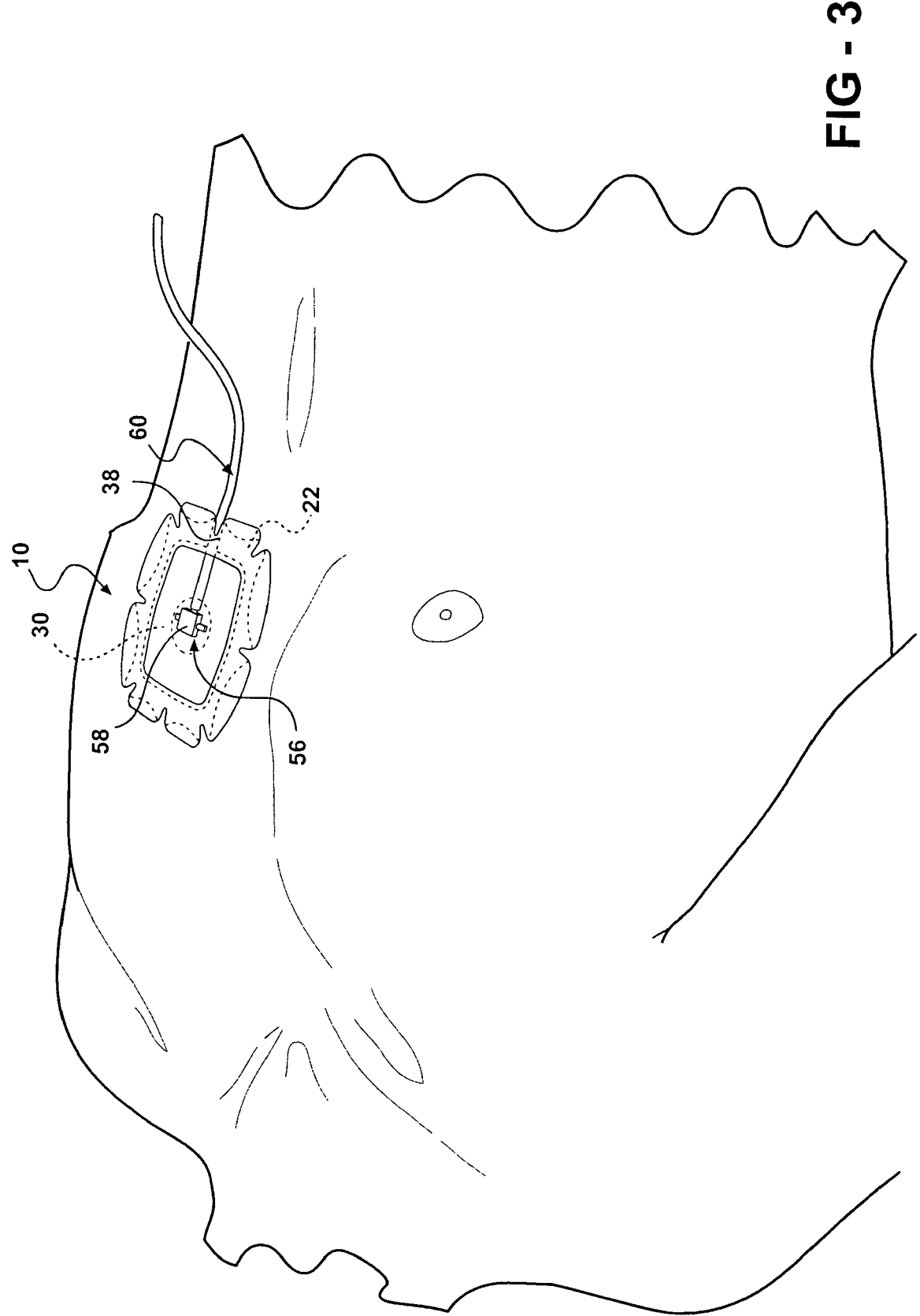
FIG. 3 is an environmental view of the window dressing of FIG. 1 illustrating the window dressing of FIG. 1 securing and protecting a huber needle and tubing on a patient.

Turning next to FIG. 3, for purposes of example the dressing 10 is shown covering and protecting a Huber infusion needle and safety guard combination 56 inserted into an implanted port at an insertion site 58 on a patient. The dressing 10 is placed over the needle and safety guard 56 as well as the insertion site 58 and adhered to the patient's skin in such a way that the adhesive-free portion 30 is on top of the needle and safety guard 56 and insertion site 58. Hence, when the dressing 10 is removed, the dressing will not stick to the needle/safety guard 56 or the insertion site 58. It can also be seen that medical tubing 60 connected to the needle/safety guard 56 is covered by the dressing 10 proximate the needle/safety guard 56. Further, a portion of the tubing 60 exiting from underneath the dressing 10 is disposed in the dressing recess 38. The recess 38 thereby receives the tubing 60 and helps to secure the tubing. The reinforcement member 22 is also disposed about the tubing 60. If the tubing 60 is pulled in any direction (up, left, right, axially, etc.), the reinforcement member 22 receives some of the pulling force, distributes the pull force over a much larger adhesive skin contact area, and resists the peeling of the dressing 10 away from the patient's skin.

Turning now to FIG. 4, in an alternative embodiment, a self-adherent window dressing 110 includes a reinforcement member 122 that is a strengthening layer locally disposed about a portion of the dressing 110. In the embodiment shown, the window dressing 110 includes a plurality of locally disposed reinforcement members 122. The window dressing 110 also includes a plurality of recesses 138. Each reinforcement member 122 is disposed about one of the recesses 138. The window dressing 110 otherwise has features similar to the first embodiment of the window dressing 10.

Figure 5:
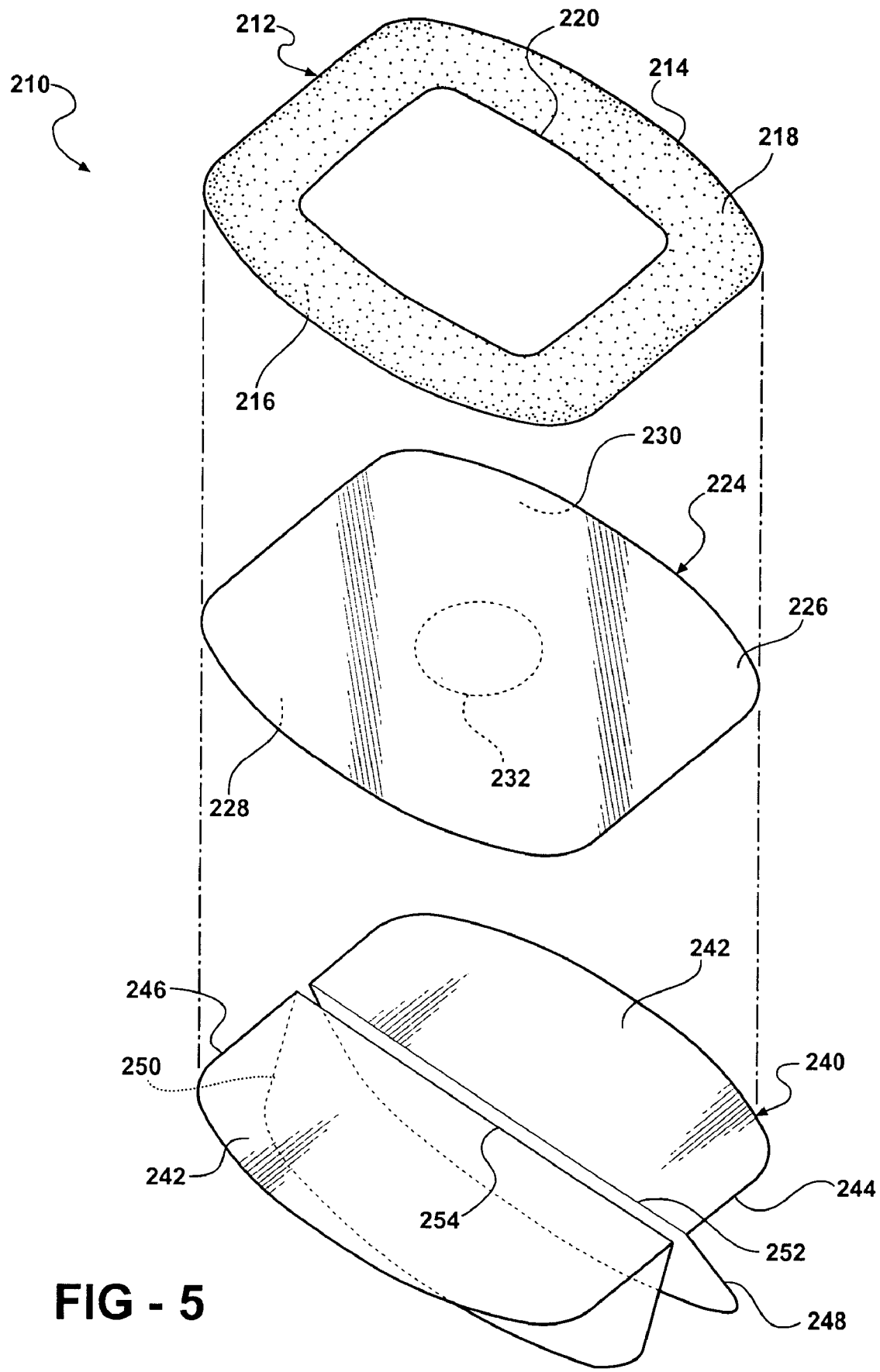
FIG. 5 is an exploded view of another alternative embodiment of a window dressing in accordance with the present invention.

With reference to FIG. 5, in another alternative embodiment of the present invention, a self-adherent window dressing 210 includes a fabric layer 212 having an adhesive side 216, an opposite non-adhesive side 218, and an opening 220 therein to allow for viewing therethrough. The dressing 210 also includes a transparent film layer 224 closing the opening 220 and having first and second opposing sides 226, 228. The film layer first side 226 is non-adhesive and is mounted on the fabric layer adhesive side 216 to close the opening 220 in the fabric layer 212. The film layer second side 228 has a skin adhering adhesive portion 230 and an adhesive-free portion 232. The adhesive-free portion 232 is disposed inwardly of the opening 220. The film layer adhesive-free portion 232 is adapted not to stick to a wound, connector, or catheter disposed between the film layer adhesive-free portion and skin.

Optionally, the window dressing 210 may include recesses such as those found in the other embodiments, although this feature is not shown in FIG. 5. The window dressing 210 may also include a release liner 240. The release liner 240 may be a butterfly-type release liner, may have first and second pieces 244, 246, and may have features similar to the release liner of the first embodiment.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A self-adherent window dressing comprising:
   a fabric layer bounded by an edge, said fabric layer having an adhesive side, an opposite non-adhesive side, and an opening therein to allow for viewing therethrough;
   a reinforcement member adhered to at least a portion of said fabric layer, said reinforcement member distributing pull forces over a larger area and resisting peeling of said dressing from a patient's skin;
   at least one recess in said fabric layer edge, said reinforcement member is disposed about and coincident with said at least one recess; and
   a transparent film layer closing said opening and having first and second opposing sides;
   said film layer first side being non-adhesive and being mounted on said fabric layer adhesive side to close said opening in said fabric layer;
   said film layer second side having a skin adhering adhesive portion and an adhesive-free portion, said adhesive-free portion being disposed inwardly of said opening;
   whereby said film layer adhesive-free portion is adapted not to stick to a wound, connector, or catheter disposed between said film layer adhesive-free portion and skin.

2. The window dressing of claim 1, wherein said film layer adhesive-free portion is generally centered within said opening.

3. The window dressing of claim 1, wherein said adhesive-free portion has one of a circular, oval, or rectangular shape.

4. The window dressing of claim 1, wherein said film layer generally extends to said fabric layer edge.

5. The window dressing of claim 1, wherein said reinforcement member is a continuous strengthening layer extending around a periphery of said dressing.

6. The window dressing of claim 1, wherein said reinforcement member is a strengthening layer locally disposed about a portion of said dressing.

7. The window dressing of claim 1, wherein said reinforcement member is disposed between said opening and said fabric layer edge.

8. The window dressing of claim 1, including a plurality of reinforcement members.

9. The window dressing of claim 1, including a release liner having a releasable side contacting said film layer skin adhesive portion, said release liner generally extending to said fabric layer edge.

10. The window dressing of claim 9, wherein said release liner includes a first piece and a second piece, said first and second pieces being folded such that each of said first and second pieces have a tab formed by the fold; whereby one of said pieces is releasable from said dressing without tampering with the other of said pieces.

11. The window dressing of claim 1, wherein said reinforcement member is a netting material.

12. A self-adherent window dressing comprising:
    a fabric layer bounded by an edge, said fabric layer having an adhesive side, an opposite non-adhesive side, and an opening therein to allow for viewing therethrough;
    a reinforcement member adhered to at least a portion of said fabric layer, said reinforcement member distributing pull forces over a larger area and resisting peeling of said dressing from a patient's skin;
    at least one recess in said fabric layer edge, said reinforcement member is disposed about and coincident with said at least one recess; and
    a transparent film layer closing said opening and having first and second opposing sides;
    said film layer first side being non-adhesive and being mounted on said fabric layer adhesive side, and said film layer second side including a skin adhering adhesive thereon.

13. The window dressing of claim 12, wherein said reinforcement member is a continuous strengthening layer extending around a periphery of said dressing.

14. The window dressing of claim 12, wherein said reinforcement member is a strengthening layer locally disposed about a portion of said dressing.

15. The window dressing of claim 12, wherein said reinforcement member is disposed between said opening and said fabric layer edge.

16. The window dressing of claim 12, including a plurality of reinforcement members.

* * * * *